United States Patent [19]

Herrmann et al.

[11] Patent Number: 4,649,196
[45] Date of Patent: Mar. 10, 1987

[54] PROCESS FOR THE MANUFACTURE OF RACEMIC (R,R; S,S) ASOCAINOL

[75] Inventors: Wolfgang Herrmann, Merzhausen; Gerhard Satzinger, Denzlingen, both of Fed. Rep. of Germany

[73] Assignee: Warner-Lambert Company, Morris Plains, N.J.

[21] Appl. No.: 730,124

[22] Filed: May 3, 1985

[30] Foreign Application Priority Data

May 23, 1984 [DE] Fed. Rep. of Germany ....... 3419099

[51] Int. Cl.⁴ .......................................... C07D 225/08
[52] U.S. Cl. .................................................. 540/479
[58] Field of Search .................... 260/239 D; 540/479

[56] References Cited

U.S. PATENT DOCUMENTS 4,415,495 11/1983 Satzinger et al. .............. 260/239 D

FOREIGN PATENT DOCUMENTS 0035360 9/1981 European Pat. Off. .

OTHER PUBLICATIONS

Journal of the American Chemical Society, 80, Jan. 20, 1958, Easton, Pa. USA; J. A. Berson et al. "Asymmetric Induction Studies with Optically Active Biphenyls, the Reactions of Phenylglyoxylates of the Phenylglyoxylates Series with Methylmagnesium Iodide"; pp. 445–451.

Primary Examiner—Glennon H. Hollrah
Assistant Examiner—David B. Springer
Attorney, Agent, or Firm—Elizabeth M. Anderson

[57] ABSTRACT

A process for the preparation of racemic asocainol in the (R,R; S,S)-form and (−)-asocainol in the (S,S)-form as well as the pharmacologically compatible salts thereof is herein described on the basis of a thermal rearrangement of the inactive (R,S)-diastereomer to the (S,S)-form.

Racemic (±)-asocainol and the (−)-enantiomer are potent antiarrhythmic agents and local anesthetics.

1 Claim, 2 Drawing Figures

PROCESS FOR THE MANUFACTURE OF RACEMIC (R,R; S,S) ASOCAINOL

BACKGROUND AND FIELD OF THE INVENTION

Asocainol [(+)-2,12-dimethoxy-1-hydroxy-7-methyl-6-phenethyl-5,6; 8,9-tetrahydro-7H-dibenz(d,f)azonine]— is a pharmaceutical agent known from DE-PS 30 07 710, which blocks nerve impulses and is particularly suitable for use as a local anesthetic and as an antiarrhythmic. It is therefore particularly suited for surface anesthesia and for the therapy of cardiac dysrhythmia.

The object of the present invention is to improve the synthesis of (+)-asocainol in a way to prevent the occurrence of inactive and undesired side products, or to convert these inactive and undesired side products into useful products.

This object was resolved by the thermal isomerization of a diastereomer of the (+)-asocainol to the (−)-enantiomer of this substance and the formation of the racemate from the two optical antipodes.

By means of x-ray structure analysis an absolute configuration according to Formula I was determined for (+)-asocainol.

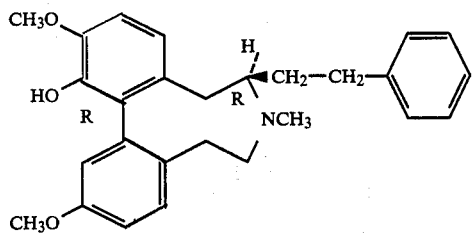

I

Theoretically asocainol may occur in four different isomeric forms caused by:
(1) The asymmetric C-atom in Position 6
(2) A biphenyl asymmetry in the bond C13a–C13b.

The biphenyl asymmetry is caused by the two phenyl rings not being on one plane but arranged almost vertically to one another. The following configurations are therefore conceivable:

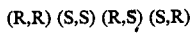

(R,R) (S,S) (R,S) (S,R)

The pairs (R,R) and (S,S) and the pairs (R,S) and (S,R) are enantiomers theoretically forming one racemate each. Enantiomers have identical chemical structures. They are alike in all their physical properties with the exception of the sign for the rotation of the polarized light.

Also their chemical behavior towards achiral reagents is alike. With chiral compounds, however, enantiomers react differently which may be useful for separating them from racemic mixtures.

In the case of asocainol there is not only optical "isomerism" but also diastereomerism. The characteristic of diastereomers is that they are hot mirror images of each other.

Thus the pairs (R,R) and (S,S) are diastereomeric to the pairs (S,R) and (R,S). Likewise the racemate (R,S; S,R) is a diastereomer of racemate (S,R; R,S). The configuration first mentioned with the pair always relates to the biphenyl asymmetry, the second to the asymmetric C-atom in Position 6. (S,R) means:
S-configuration with regard to the biphenyl asymmetry, R-configuration on C6.

When synthesizing (+)-asocainol according to Example 10 of DE-PS 30 07 710 from natural thebaine (Merck Index 1976 Number 8988) the hydrochloride is produced in a yield of 21% of theory. In addition to the desired (+)-asocainol with the configuration (R,R) there results in an extremely unfavorable weight ratio of 1:3.25 the inactive and therefore useless diastereomer with the configuration (R,S). All previous attempts to shift this unfavorable isomer ratio by changing the synthetic parameters, e.g., with other solvents and varying temperatures, quantity ratios or concentrations, in order to increase the yield of the desired isomer were unsuccessful. Surprisingly it has now been found that the undesirable diastereomer (R,S) to some extent rearranges itself in the biphenyl system when heated above its melting point (138° C.), so that 40% of the (R,S) diastereomers can be converted to the (S,S) enantiomers. Although it was possible to racemize (+)-asocainol, the (S,S)-isomer cannot be converted to (+)-asocainol with (R,R)-configuration. Such conversion is not even in part possible so that at first there was no way to find a meaningful use for the "false" enantiomer of (+)-asocainol. However, pharmacological investigations surprisingly showed that the (S,S)-isomer also possesses antiarrhythmic activity. The synthesis of the racemate (R,R; S,S) from equal parts of (+)-asocainol in (R,R)-form and (S,S)-isomers gave a surprising pharmacologic result. Instead of the additive effect expected a marked synergistic antiarrhythmic effect was found [Arch. Pharmacol. Suppl., 319 (1982) Nr. 145]. This did not only solve the problem of what to do with the unusable (R,S)-isomer but quite surprisingly also improved the effectiveness of the (+)-asocainol according to DE-PS 30 07 710. The solution of the problem according to the invention is thus even more valuable since there was no way known to obtain the (S,S)-enantiomer of the (+)-asocainol.

Theoretically conceivable were the following ways to prepare the (S,S)-isomer;
(1) Inversion of the (R,R)-isomer to the (S,S)-configuration;
(2) preparation by Grignard synthesis according to DE-PS 30 07 710 using "unnatural" thebaine.

Both ways proved not to be practicable. So far it has been impossible to produce an inversion and "unnatural" thebaine as the enantiomer of the natural thebaine is not available for a process of any technical use. The "direct" production of the racemate by racemization of (+)-asocainol or by Grignard reaction out of racemic thebaine was equally impossible since racemic thebaine is technically inaccessible and (+)-asocainol cannot be racemized by known means.

Since, as mentioned above, any better activity could not be expected from the racemate (R,R; S,S) as compared with (+)-asocainol no further attempts were made to produce and test the racemate. Only the unexpectedly found possibility to convert the (R,S)-configuration thermally into the (S,S)-configuration led to the discovery of the surprising synergistic effect of the asocainol enantiomers (R,R) and (S,S) combined to the racemate.

The following structural Diagram II shows the four possible configurations and the symbols of their racemates.

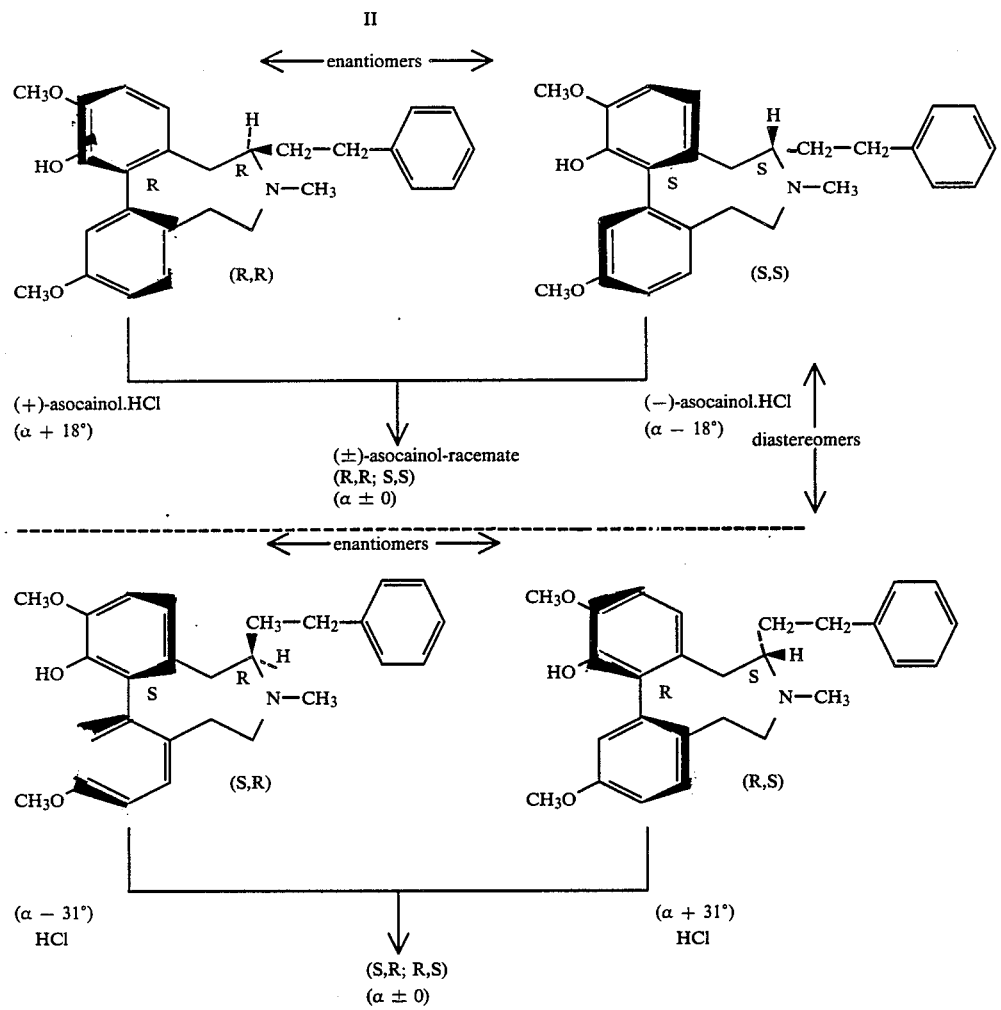

SUMMARY OF THE INVENTION

Accordingly the present invention is a process for the preparation of racemic asocainol by Grignard reaction of natural thebaine (The Merck Index 1976, Number 8988) with a phenethyl magnesium halide, especially chloride or bromide, and separation of the resulting diastereomers (R,R) and (R,S) in a previously known manner by fractional crystallization of the hydrochlorides from a lower alcohol, preferably isopropanol, characterized by the separated diastereomer (R,S) being at least partially rearranged to the enantiomer (S,S) by heating to 130°-200° C., the rearranged (S,S)-enantiomer being separated from the unchanged (R,S)-diastereomer in a previously known manner, by dissolving in a solvent the (S,S)-enantiomer preferably with (+)asocainol of the (R,R)-form as base or salt, in the molar ratio of 1:1, and by isolating the resulting racemate (R,R; S,S) in the form of its base or its pharmacologically compatible salts.

DETAILED DESCRIPTION

Figure 1:
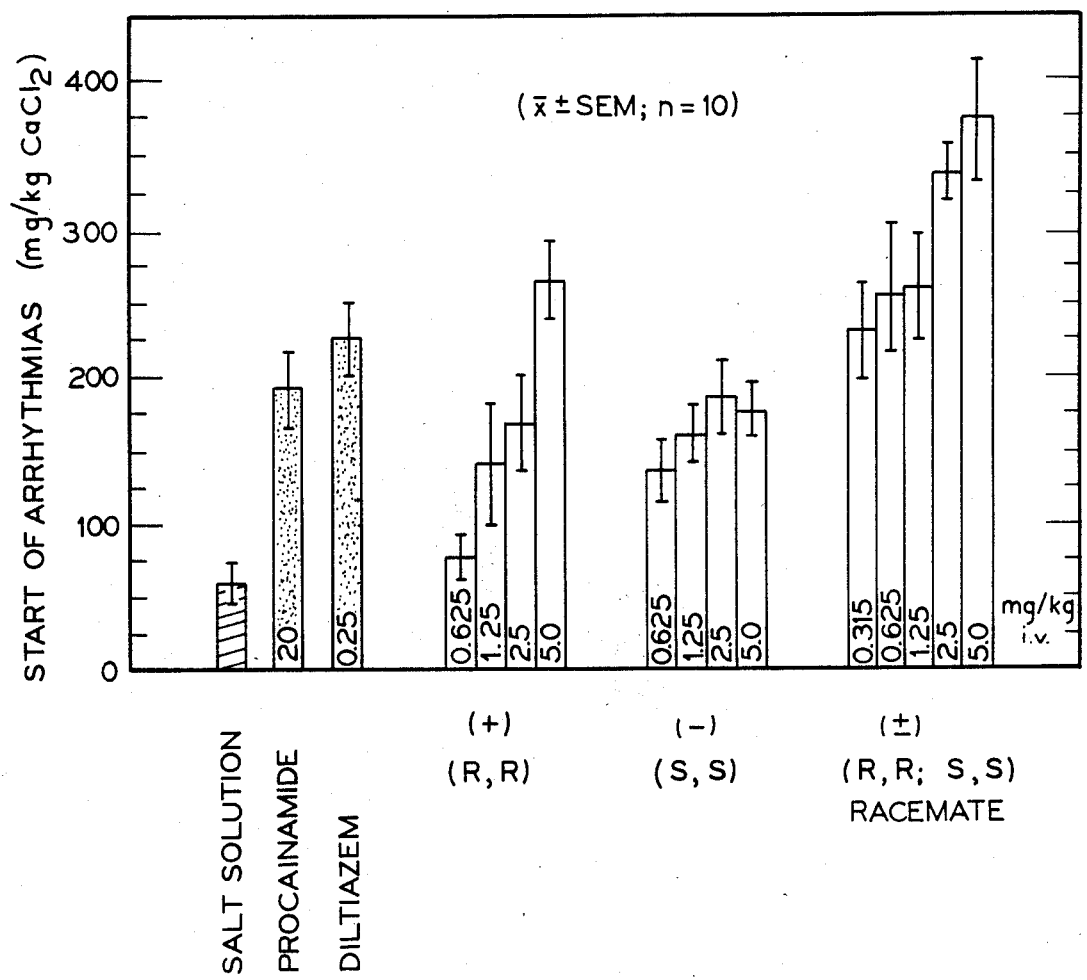

The thermal rearrangement of the diastereomer (R,S) may either be effected without solvent or in inert organic solvents having a high boiling point, i.e., at least 130° C., such as e.g., dimethylformamide, xylene, ligroin, or chlorobenzene. In that case the thermal rearrangement may also be effected slightly below the melting point of the diastereomer, e.g., at 130° C. The separation of the mixture formed by the thermal isomerization, consisting of the (R,S) and the (S,S) form, is brought about by fractional crystallization of a salt, preferably a hydrochloride, from an organic solvent, preferably an aliphatic ester with up to ten carbon atoms, an aliphatic alcohol with up to six carbon atoms, or mixtures of these solvents.

The preparation of the racemate of the asocainol is effected by dissolving equal parts of the dextrorotatory and levorotatory enantiomers (R,R) and (S,S), preferably in the form of the free bases, in an inert solvent, preferably in a halogen hydrocarbon such as methylene chloride, chloroform, carbon tetrachloride or dichloroethylene, an aliphatic alcohol with up to six carbon atoms, preferably in ethanol or isopropanol, or an aliphatic ester or ether with up to ten carbon atoms, and by precipitating the racemate as a salt either by the addition of acids, preferably gaseous hydrochloric acid, or as a free base by evaporation of the solvent.

It is equally possible to precipitate the racemate by cooling or by means of a solvent with poor dissolving properties for the racemate such as, e.g., petroleum ether or lower aliphatic ethers.

The conversion of the free bases of the racemic asocainol into its pharmacologically acceptable acid addition salt is effected by means of reaction with an inorganic or organic acid, such as, e.g., hydrochloric acid, sulphuric acid, phosphoric acid, hydrobromic acid, acetic acid, fumaric acid, oxalic acid, lactic acid, citric acid, malic acid, salicyclic acid, malonic acid, maleic acid, succinic acid, or ascorbinic acid. Special preference is accorded to hydrochloric acid, phosphoric acid, and citric acid.

For the preparation of pharmaceutical agents the active ingredients are processed with the usual additives and liquid or solid carriers. Racemic asocainol may be administered in a broad range of doses in liquid or solid form or parenterally.

The usual additives for liquid forms are, e.g, tartrate and citrate buffers, ethanol, complex formers (such as ethylene-diaminetetraacetic acid and its nontoxic salts) as well as highly molecular polymers (such as liquid polyethylene oxide) to regulate the viscosity. Solid carriers are, e.g., starch, lactose, mannite, methylcellulose, talcum, highly disperse silicic acids, higher-molecular fatty acids (such as stearinic acid), gelatin, agar-agar, calcium phosphate, magnesium stearate, animal and vegetable fats, solid high-molecular polymers (such as polyethylene glycol); preparations suitable for oral administration may also contain flavors and saccharins.

The following examples serve to further illustrate the invention.

EXAMPLE 1

Preparation of
(+)-6,7,8,9-tetrahydro-2,12-dimethoxy-7-methyl-6(e')-phenethyl-5H-dibenz(d,f)azonin-1-ol hydrochloride [(R,R)-form]

(a) After evacuating and rinsing the whole apparatus with nitrogen, 528.0 g (21.7 mol) magnesium chips and 2.0 liter anhydrous tetrahydrofuran are introduced in a 50 l glass reaction vessel. Adding a small quantity of iodine the mixture is heated to 50° C. and 3714.0 g (20.0 mol)=2710.94 ml phenethylbromide in 5.0 l toluene are added at 50°-60° C. over a period of 2.5 hours.

After completion of the dropping-in process the mixture is stirred out at 50°-60° C. for 30 minutes and subsequently heated to reflux for one hour.

Under good reflux and while stirring 3125.0 g (10.036 mol) thebaine dissolved in 24.0 l toluene at 95° C., are poured in under nitrogen over a period of 20 minutes. The mixture is then stirred out under reflux for two hours.

After cooling to 50° C. the reaction mixture is stirred onto 20 l water and 30 l ice, adjusted to a pH of 7.0 with 750 ml glacial acetic acid, and the phases separated. The aqueous phase is stirred out with altogether 45 l methylene chloride; the combined organic phases are washed with water and subsequently dried over a mixture of sodium sulfate and silica gel. After filtration through a single-layer filter the filtrate is washed with methylene chloride and reduced to dryness under a vacuum. As the residue are obtained 4065.0 g crude base=97.0% of theory in relation to thebaine.

The composition of the crude base is tested by means of HPLC. The content of the desired isomers is 20-23%, the content of the diastereomeric compound 65 to 70%.

In a 100-l container are dissolved 4065.0 g (9.736 mol) crude base in 21.68 l ethyl acetate and 3.42 l isopropanol at 60°-70° C. and then the hydrochloride of the (R,R)-form (up to pH 2-3) is precipitated with a freshly prepared solution of 0.356 kg (9.74 mol) gaseous hydrochloric acid in 2.0 l isopropanol. While stirring the mixture is cooled to 17°-18° C. by means of cold water over a period of one to two hours and the precipitate crystallisate filtered off, washed with cooled isopropanol, and dried in a circulation drying cabinet at 70°-90° C. Obtained are 800 g colorless (+)-6,7,8,9-tetrahydro-2,12-dimethoxy-7-methyl-6(e')-phenethyl-5H-dibenz(d,f)azonin-1-ol hydrochloride (17.5% of theory). M.p.: 229.5° C.; HPLC content: >99%; $(\alpha)_D = +17.8°$ C. (c=1/H$_2$O).

(b) A Grignard-solution is prepared from 625 g (25.7 mol) magnesium and 3353 g (23.8 mol) phenethylchloride in 7.5 l tetrahydrofuran. A 90° to 100° C. hot solution of 3516 g (11.2 mol) thebaine in 30 l toluene is then added within 30 minutes at a temperature of 105°-110° C. The reaction mixture is then kept for another hour at about 110° C. (weak reflux), then cooled to 40°-50° C. and poured into 40 l water. After acidifying with acetic acid (pH 6-7) the organic layer is separated and the aqueous phase extracted with 35 l toluene. The combined toluene-portions are dried with sodium sulfate and evaporated in a vacuum to an amount of about 20 l. At 50° C. a solution of 183 g of hydrogenchloride-gas in 800 ml isopropanol is added and the solution is cooled to 15° C. After 2.5 hours the crystals formed are separated by centrifugation, washed, and dried.

Yield: 1.8 kg R,R-form=35% of theory, purity after HPLC=91%.

From the mother liquor according to (a) 1.6 kg=36% of theory of the R,S-form may be separated. HPLC-content 91%.

EXAMPLE 2

Isolation of
(+)-6,7,8,9-tetrahydro-2,12-dimethoxy-7-methyl-6(a')-phenethyl-5H-dibenz[d,f]azonin-1-ol [(R,S)-form]

The mother liquor from the hydrochloride precipitation according to Example 1 is reduced to dryness under vacuum. The yield is 4270.0 g residue. This residue is dissolved in 30 l methylene chloride, 15 l water, and 0.75 l concentrated hydrochloric acid. After briefly stirring the phases are separated and the aqueous phase stirred out twice with five liter portions of the methylene chloride. The base is released from the combined methylene chloride phases by the addition of 15.0 l water and 1.5 l concentrated ammonia. After separation of the organic phase the aqueous phase is stirred out twice with five liter portions of methylene chloride and is then discarded.

The combined methylene chloride phases are washed with 15.0 l water and dried over sodium sulfate and silica gel. After filtration the solvent is distilled off under vacuum. The residue so obtained is recrystallized directly from 65.0 l methanol. The crystallisate is allowed to stand overnight, is cooled to 0° C. while stirring slowly, and centrifuged. The residue is dried in a circulation drying cabinet at 70°-80° C. As the crystallisate are obtained 1.70 kg almost colorless (+)-6,7,8,9-tetrahydro-2,12-dimethoxy-7-methyl-6(a')-phenethyl-5H-dibenz[d,f]azonin-1-ol (40.5% of theory). By reduction of the mother liquor and repeated recrystallization of the second crystallisate another 0.437 kg of base are obtained (10.3% of theory). Thus the total yield is 2.137 kg=50.8% of theory.

M.p.: 138° C.; HPLC purity: >98%; $(\alpha)_D = +76°$ C. (c=1/MeOH).

EXAMPLE 3

Partial Rearrangement to
(−)-6,7,8,9-tetrahydro-2,12-dimethoxy-7-methyl-6(e')-phenethyl-5H-dibenz[d,f]azonin-1-ol hydrochloride [(S,S)-form]

To a 10-l flanged flask with nitrogen lead, cooler, thermometer, stirrer, and mushroom heater 2770 g (6.634 mol) of the (R,S)-base from Example 2 are heated under nitrogen to a temperature of over 150° C. for several hours. After cooling the reaction mixture to about 100° C., 6.0 l ethyl acetate are added to the melt while stirring thoroughly. During this process the temperature drops to 40° C. The solution is mixed with 400 g silica gel 60 and 200 g active earth and stirred for one hour.

After the filtration the residue from the filtration is washed with 10.0 l ethyl acetate, the whole filtrate is diluted with 6.0 l ethyl acetate and 2.2 l isopropanol and then mixed with 10% ethyl acetate/HCl solution until a pH of 2-3 is obtained. After cooling to 15° C. the crystallisate is sucked off, washed with ethyl acetate, and then dried in the circulation drying cabinet at 80°-90° C. The yield is 1037.0 g colorless (−)-6,7,8,9-tetrahydro-2,12-dimethoxy-7-methyl-6(e')-phenethyl-5H-dibenz[d,f]azonin-1-ol hydrochloride (34.4% of theory).

M.p.: 229.5° C.; HPLC purity: >99%; $(\alpha)_D = -17.5°$ C. (c=1H$_2$=).

The mother liquor from the hydrochloride precipitation still contains about 60% of the (R,S)-form used. The largest part of this substance may be recovered.

EXAMPLE 4

Preparation of
(+)-6,7,8,9-tetrahydro-2,12-dimethoxy-7-methyl-6(e')-phenethyl-5H-dibenz[d,f]azonin-1-ol, asocainol racemate In a 30-l vessel with stirrer are dissolved together 1030.0 g (2.268 mol) of the (R,R)-form (Example 1) and 1030.0 g (2.268) of the (S,S) form (Example 3) as hydrochloride in 20.0 l water. Then are added 5.0 l methylene chloride and the solution is subsequently alkalinized with concentrated ammonia. The phases are separated and the aqueous phase stirred about three times with 5.0-l portions of methylene chloride. The combined methylene chloride extracts are washed with water, dried over sodium sulfate and silica gel, and after filtration reduced to dryness under vacuum at 50° C. bath temperature. As residue 1905.0 g racemic base are obtained.

$(\alpha)_D = \pm 0$ (c=1/MeOH).

The base then is dissolved in 18.5 l ethyl acetate and 1.85 l isopropanol, filtered through a folded filter, and the hydrochloride precipitated with 10% ethyl acetate HCl-solution (pH 2-3). Centrifugation after cooling to 15° C. and subsequent drying in the circulation drying cabinet at 80° C. The yield is 1844.0 g (±)-6,7,8,9-tetrahydro-2,12-diemthoxy-7-methyl-6-(e')-phenethyl-5H-dibenz[d,f]azonin-1-ol hydrochloride=racemic asocainol HCl. M.p.: 214° C.; HPLC purity: >99.5%; $(\alpha)_D = \pm 0°$ C. (c=1/H$_2$O).

For the preparation of the base a 5% aqueous solution of the hydrochloride is alkalinized with a solution of sodium hydroxide and the base formed is extracted with dichloromethane or chloroform. The residue obtained after distilling off the organic solvent is recrystallized from ethanol. Yield is about 90%.

M.p.: 118°-119° C.; HPLC-purity 99%.

EXAMPLE 5

(±)-Asocainol-Phosphate

Thirty-eight g (0.091 mol) (±)-asocainol base are dissolved in 940 ml ethanol while heating. Subsequently a solution of 8.91 g (0.091 mol) phosphoric acid in 18 ml ethanol is added dropwise while stirring. After cooling the resultant residue is isolated.

Yield: 36 g (76.7% of theory)
M.p.: 147.2° C.; HPLC purity: >99%.

EXAMPLE 6

(±)-Asocainol-Citrate

Fifty g (0.12 mol) (±)-asocainol base are dissolved in 2.5 l diethyl ether at room temperature. While stirring a solution of 25.22 g (0.12 mol) citric acid monohydrate in 100 ml ethanol is added dropwise. The resultant residue is sucked off and dried.

Yield: 73 g (99.7% of theory).
M.P.: 93° C.; HPLC purity: >99%.

The following reference tests demonstrate the pharmacological activity of asocainol racemate.

TEST 1

Arrhythmias in the Rat Induced by CaCl$_2$

Raised extracellular calcium levels result in an increased excitability of the myocardium and at the same time inhibit the automaticity.

When anesthesized rats are given infusions of CaCl$_2$ solution there first results a brief tachycardiac phase and then bradycardiac arrhythmias with ventricular extrasystoles occur. By injecting antiarrhythmic agents before starting the CaCl$_2$ infusion it is possible to increase the amount of CaCl$_2$ necessary to start the arrhythmias.

Asocainol racemate was tested in doses between 0.315 to 5.0 mg/kg IV in comparison with its enantiomers, and effected an increase in the arrhythmogenic CaCl$_2$ quantity (FIG. 1) dependent upon the dose. Compared with its enantiomers and reference substances the most potent action would be achieved with asocainol racemate in these tests.

FIG. 1 describes the effect of asocainol racemate (R,R; S,S) form and of its enantiomers [(R,R)-form and (S,S)-form] with arrhythmias in anesthesized rats induced by CaCl$_2$ (1.5 g/kg IP urethane). The Intravenous administration of the active substances began before starting the CaCl$_2$ infusion (10 mg/min). The doses stated relate to the free bases.

TEST 2

Arrhythmias in the Guinea Pig Induced by Quabain

Intoxications with cardiac glycosides produce in the heart disturbances of the impulse formation and conduction. While the sino-atrial node and the impulse conduction are inhibited (particularly at the atrioventricular node), the automatism of the Purkinje's fibers is increased.

After a bradycardiac phase disturbances of the atrioventricular conduction occur which are followed by ventricular tachycardias and finally ventricular fibrillation.

In anesthesized guinea pigs the infusion of 180 μg/kg quabain led to largely tachycardiac arrhythmias with polymorphous extrasystoles.

Upon completion of the infusion the arrhythmic effect of quabain usually had completely developed within five minutes, then the test substance was injected intravenously if less than 50% of cardiac activity was normal sinus rhythm. The activity of the substances was monitored by means of ECG for 15 minutes. As the measure for the antiarrhythmic activity served for proportion of normal sinus rhythm during the time measured, i.e., the excitation in which a normal QRS complex followed to a p-wave.

Figure 2:
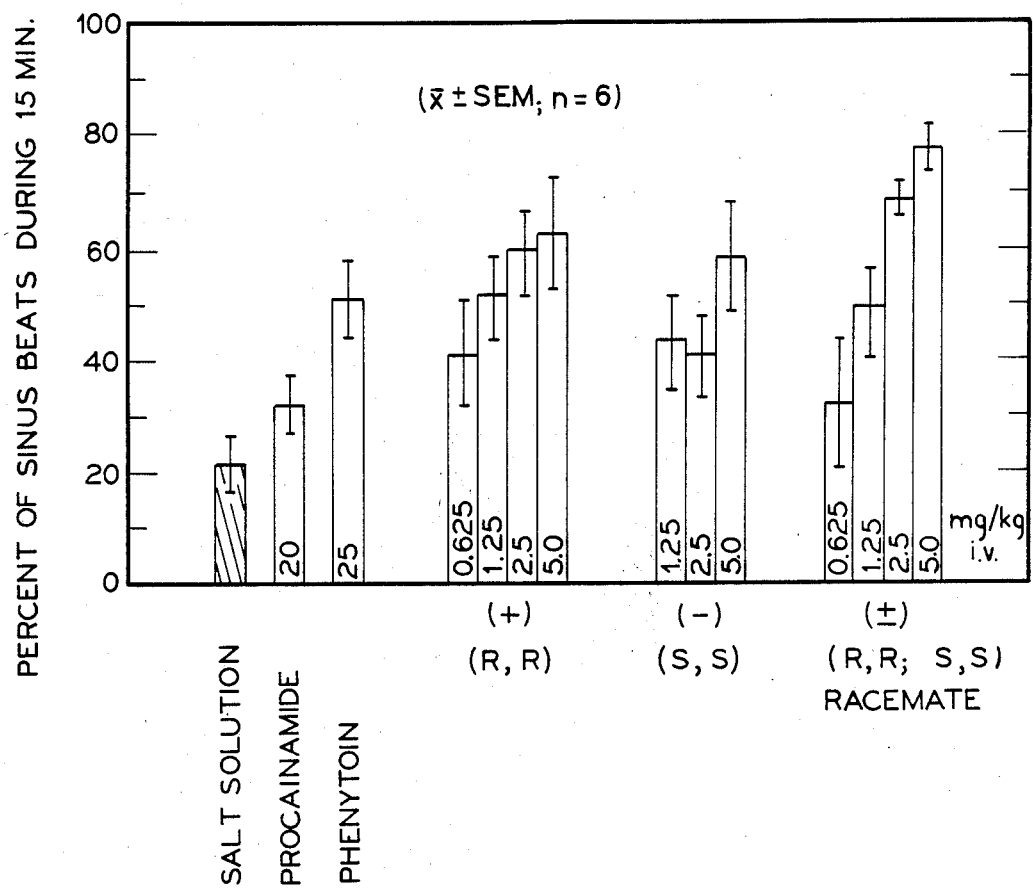

FIG. 2 shows the results. In these 1.25 mg/kg asocainol racemate were about equally effective as 25 mg/kg phenytoin, which is clinically used in the case of arrhythmias due to intoxication with cardiac glycosides. In these tests, too, asocainol racemate proved to be considerably more potent than its two enantiomers.

FIG. 2 illustrates the effectiveness of asocainol and its enantiomers in arrhythmias induced by quabain as demonstrated in guinea pigs. The antiarrhythmic activity was determined as a percent share in the normal sinus rhythm during 15 minutes of measurements after intravenous application of the substance (doses related to the free base of the active substance).

We claim:
1. A process for the preparation of racemic asocainol which comprises:
(a) reacting natural thebaine with phenethyl magnesium bromide;
(b) separating the diastereomers (R,R) and (R,S) by fractional crystallization of the hydrochlorides from a lower alkanol;
(c) heating the diastereomer; (R,S) between 130° and 200° C. in an inert organic solvent or above 138° C. in the absence of a solvent to give partial conversion to the (S,S) enantiomer by thermal rearrangement;
(d) separating by fractional crystallization of the hydrochlorides as in step (b) the (S,S) enantiomer from the (R,S) diastereomer;
(e) dissolving equimolar amounts of the (S,S) and the (R,R) enantiomer of (+)-asocainol as a base or hydrochloride or other pharamcologically acceptable salt in an inert solvent; and
(f) isolating the racemate (R,R; S,S) as its free base or its pharmacologically acceptable acid addition salt.

* * * * *